(12) United States Patent
Baek

(10) Patent No.: US 10,716,925 B2
(45) Date of Patent: Jul. 21, 2020

(54) MICRO-NEEDLE AND METHOD OF MANUFACTURING THE MICRO-NEEDLE

(71) Applicant: Sun Young Baek, Seoul (KR)

(72) Inventor: Sun Young Baek, Seoul (KR)

(73) Assignee: QuadMedicine, Seongnam-si (KR)

( * ) Notice: Subject to any disclaimer, the term of this patent is extended or adjusted under 35 U.S.C. 154(b) by 67 days.

(21) Appl. No.: 15/354,059

(22) Filed: Nov. 17, 2016

(65) Prior Publication Data

US 2017/0368321 A1 Dec. 28, 2017

(30) Foreign Application Priority Data

Jun. 23, 2016 (KR) .................... 10-2016-0078351

(51) Int. Cl.
| | | |
|---|---|---|
| *A61M 37/00* | (2006.01) | |
| *B29C 41/02* | (2006.01) | |
| *B29L 31/00* | (2006.01) | |

(52) U.S. Cl.
CPC ......... *A61M 37/0015* (2013.01); *B29C 41/02* (2013.01); *A61M 2037/0023* (2013.01); *A61M 2037/0046* (2013.01); *A61M 2037/0053* (2013.01); *B29L 2031/7544* (2013.01)

(58) Field of Classification Search
CPC .. A61M 2037/0023; A61M 2037/0046; A61M 2037/0053; A61M 2037/003; A61M 2037/0061; A61M 2037/0015; A61M 37/0015; B29L 2031/7544; B29C 41/02
See application file for complete search history.

(56) References Cited

U.S. PATENT DOCUMENTS

| | | | |
|---|---|---|---|
| 8,834,423 B2 | 9/2014 | Falo, Jr. et al. | |
| 2007/0224252 A1* | 9/2007 | Trautman | A61M 37/0015 424/449 |
| 2011/0264048 A1* | 10/2011 | O'dea | A61M 37/0015 604/173 |
| 2014/0128811 A1 | 5/2014 | Ferguson et al. | |
| 2015/0157563 A1* | 6/2015 | Wirostko | A61K 45/06 424/428 |
| 2015/0374620 A1* | 12/2015 | Sugahara | A61K 47/12 604/46 |
| 2016/0158512 A1* | 6/2016 | Tamaru | B29C 39/10 604/173 |

FOREIGN PATENT DOCUMENTS

| | | |
|---|---|---|
| JP | 5879927 B2 | 5/2013 |
| KR | 10-2014-0141360 A | 12/2014 |
| KR | 10-2015-0118136 A | 10/2015 |

OTHER PUBLICATIONS

Office Action of 10-2016-0078351, dated Jul. 20, 2016.
Korean Office Action for the corresponding Korean Patent Application No. 10-2016-0078351 dated Feb. 21, 2017.

\* cited by examiner

*Primary Examiner* — Kevin C Sirmons
*Assistant Examiner* — Tezita Z Watts
(74) *Attorney, Agent, or Firm* — Sughrue Mion, PLLC

(57) ABSTRACT

Disclosed is a micro-needle including a tip formed using medicine that penetrates into the skin and melts therein; and at least one guide groove each in a stepped shape inward from the outer surface of the tip, and provided to the tip. The micro-needle configured as above may be used to administer a fixed quantity of medicine within a relatively short period of time. Also, since a guide space stepped based on the tip is provided to a base that supports the tip, a large amount of medicine may easily penetrate into the skin.

17 Claims, 8 Drawing Sheets

FIG. 4

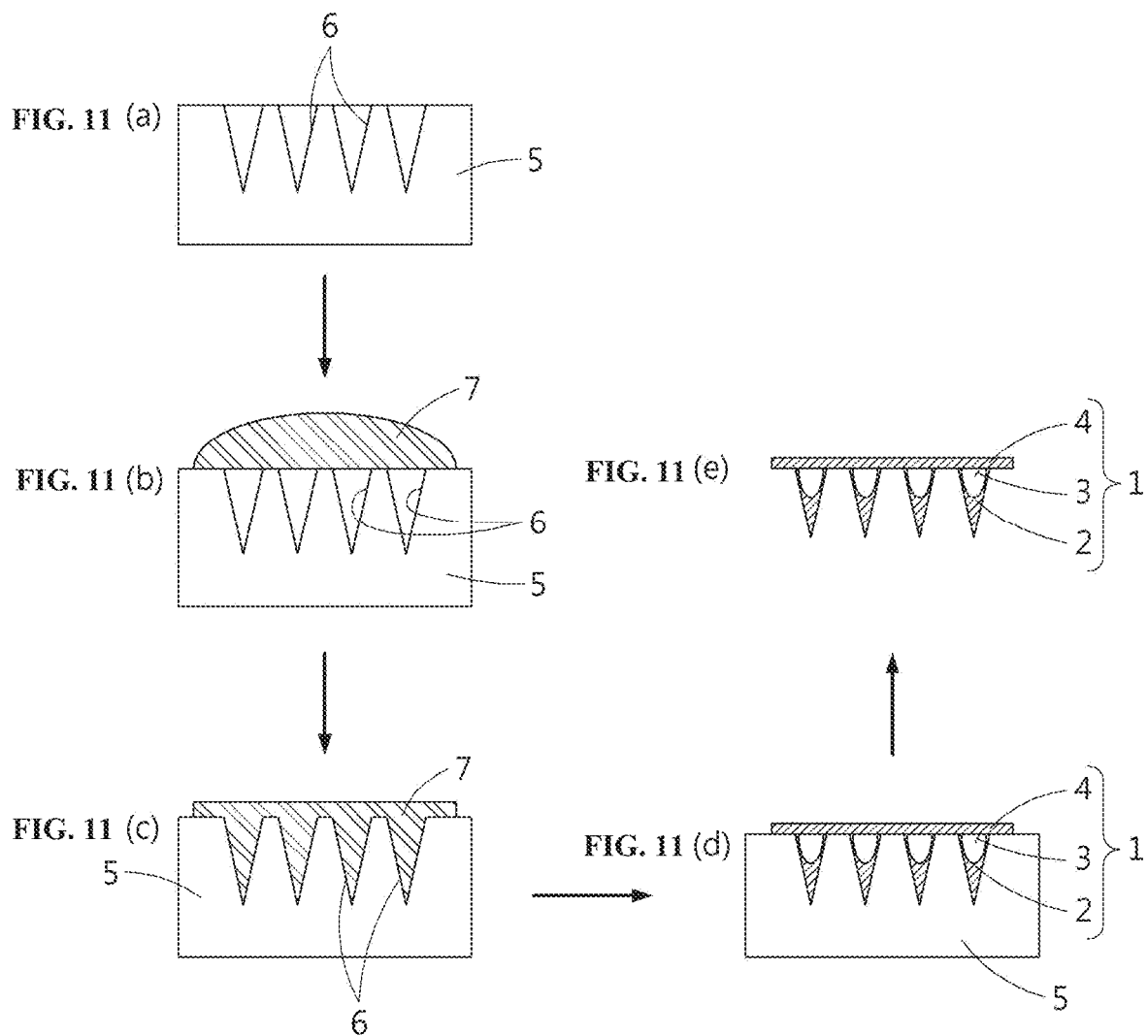

MICRO-NEEDLE AND METHOD OF MANUFACTURING THE MICRO-NEEDLE

CROSS-REFERENCE TO RELATED APPLICATION

This application claims the priority benefit of Korean Patent Application No. 10-2016-0078351 filed on Jun. 23, 2016, in the Korean Intellectual Property Office, the disclosure of which is incorporated herein by reference.

BACKGROUND

1. Field of the Invention

At least one example embodiment relates to a micro-needle and a method of manufacturing the micro-needle, and more particularly, to a micro-needle capable of efficiently administering a fixed quantity of medicine within a relatively short period of time and a method of manufacturing the micro-needle.

2. Related Art

A transdermal drug delivery scheme has some constraints in a size of transferable drug molecular weight. Accordingly, a variety of active transdermal drug delivery schemes are currently proposed. Here, a method using a micro-needle that passes through the dead skin cell and directly administers medicine to a skin layer receives the most attention. In the recent times, a melting micro-needle has been developed based on a water-soluble polymer, which has lead to developing a method of administering medicine at the same at which a tip penetrates into the skin.

Since the melting micro-needle melts in body fluid after being administered to the skin, the melting micro-needle may have a relatively excellent administration capability. However, a relatively long period of time, for example, 30 minutes or more is required to completely deliver the medicine contained in the tip. Due to such a long period of melting time, when the melting micro-needle is removed after a determined administration time, a tip of the micro-needle administered to the inside of skin may be removed in a partially non-melted state.

Since the medicine contained in the tip depends on complete melting of the tip, the fixed quantity of medicine may not be readily delivered to the skin. Accordingly, a variety of researches on a method capable of enhancing the administration capability of a micro-needle are currently continuously conducted.

The related arts may include Japanese Patent Registration No. 5879927, and U.S. Patent Publication No. 2014-0128811.

SUMMARY

Example embodiments provide a micro-needle that may efficiently administer a fixed quantity of medicine and a method of manufacturing the micro-needle.

According to an aspect of example embodiments, there is provided a micro-needle including a tip formed using medicine that penetrates into the skin and melts therein; and at least one guide groove each in a stepped shape inward from the outer surface of the tip, and provided to the tip.

A plurality of tips may be provided and may be supported by a base.

Each of the plurality of tips may be provided in a circular conic shape or a polygonal conic shape, and at least one guide groove each having a cross-section in a semicircular or polygonal shape may be provided along the outer circumference of each of the plurality of tips.

A plurality of guide grooves may be provided at equal intervals along the outer circumference of the tip, and may be configured to extend with a cross-section in a semicircular or polygonal shape toward a rear end between a front end at which the tip penetrates into the skin and the rear end that extends from the front end, based on a direction in which the tip penetrates into the skin.

A plurality of guide grooves may be spaced apart from each other at equal intervals at a location separate from a front end at which the tip penetrates into the skin toward a rear end by 80% or more based on a direction in which the tip penetrates into the skin.

A plurality of guide grooves may be spaced apart from each other along the outer circumference of the tip and provided in a multi-column and multi-row form.

The guide groove may have a cross-section in a semicircular or polygonal shape and may be configured to extend along the outer circumference of the tip.

A guide space stepped based on the tip may be provided to the base.

The tip may penetrate into the skin using at least one of air pressure, oil pressure, spring, electromagnetic field, and acupressure.

Waterproof coating may be applied to the tip.

According to another aspect of example embodiments, there is provided a method of manufacturing a micro-needle, the method including preparing medicine; and forming a tip by supplying the medicine to a mold having a tip groove. At least one inwardly stepped guide groove may be formed on the outer surface of the tip.

The preparing of the medicine may include preparing the medicine using a biocompatible material and a water-soluble additive agent.

The biocompatible material may include at least one of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide, poly vinyl pyrrolidone (PVP), hydroxypropyl methyl cellulose (HPMC), ethylcellulose (EC), hydroxypropyl cellulose (HPC), carboxymethyl cellulose, cyclodextrin, maltose, lactose, trehalose, cellobiose, isomaltose, and turanose, or may include at least one of copolymer of monomers constituting the polymer, and cellulose.

The water-soluble additive agent may include at least one of trehalose, oligosaccharide, sucrose, maltose, lactose, cellobiose, hyaluronic acid, alginic acid, pectin, carrageenan, chondroitin (sulfate), dextran (sulfate), chitosan, polylysine, collagen, gelatin, carboxymethyl chitin, fibrin, agarose, poly vinyl pyrrolidone (PVP), polyethylene glycol (PEG), polymethacrylate, hydroxypropyl methyl cellulose (HPMC), ethylcellulose (EC), hydroxypropyl cellulose (HPC), carboxymethyl cellulose, cyclodextrin, and gentiobiose.

The mold may include a structure that includes one of polydimethylsiloxane (PDMS), a type of polymer used for the mold, polyurethane, metal, an aluminum biocompatible material, water-soluble polymer, fat-soluble polymer, and amphiphilic polymer.

The fat-soluble polymer and the amphiphilic polymer may include at least one of hydroxypropyl cellulose (HPC), hydroxypropyl methyl cellulose (HPMC), polycaprolactone (PCL), polyglycolide (PGA), polylactic acid (PLA), poly lactic-co-glycolic acid (PLGA) polymer, poly vinyl pyrrolidone (PVP), polyethylene glycol (PEG), poly ethylene oxide (PEO), poly propylene oxide (PPO), poly vinyl methyl ether (PVME), PMA (poly (methyl) acrylate)s, propylene glycol, poly (ester amide), poly (butyric acid), acrylamide (acrylic amide), acrylic acid, hyaluronic acid (HA), and gelatin.

The forming of the tip may include supplying the medicine to the tip groove; and solidifying the medicine; and removing the mold. The solidifying may include forming the guide groove through a centrifugal and polymer melt process, and solidifying the medicine.

The micro-needle manufacturing method may further include applying waterproof coating to the tip.

The applying of the waterproof coating may include coating an end of the tip or the entire surface of the tip with a waterproof agent that includes a hydrophobic material or a lipid-based material using at least one of dip-coating, atomization, electro-spinning, and ultrasonic coating.

The waterproof agent may include at least one of beeswax, oleic acid, soy fatty acid, castor oil, phosphatidylcholine, d-a-tocopherol/vitamin E, corn oil mono-di-tridiglycerides, castor oil, corn oil, cottonseed oil, olive oil, peanut oil, peppermint oil, safflower oil, sesame oil, soybean oil, hydrogenated vegetable oil, hydrogenated soybean oil, caprylic/capric triglycerides derived from coconut oil or palm see oil, phosphatidylcholine, polyethylene (PE), polypropylene (PP), polytetrafluoroethylene (PTFE), polymethylmethacrylate (PMMA), ethylene vinyl acetate (EVA), polycaprolactone (PCL), polyurethane (PU), polyethylene terephthalate (PET), polyethylene glycol (PEG), polyvinyl alcohol (PVA), poly lactide (PLA), poly lactic-co-glycolic acid (PLGA) polymer, polyglycolide (PGA), wax (paraffin cholesterol), glycerin, chitin, lecithin, animal beef tallow, vegetable stearin, low-grade saturated fatty acid, monosaturated fatty acid, tristearins, fatty acid mineral salt (zinc, calcium, magnesium stearate), and fatty acid zinc salt (stearic acid, palmitic acid, lauric acid), or includes the mixture thereof.

The forming of the tip may include forming a plurality of tips each in a conic shape or a polygonal conic shape, and forming at least one guide groove each having a cross-section in a semicircular or polygonal shape along the outer circumference of each of the plurality of tips.

The forming of the tip may include forming a plurality of guide grooves to be spaced apart from each other at equal intervals at a location separate from a front end at which the tip penetrates into the skin toward a rear end by 80% or more based on a direction in which the tip penetrates into the skin, and a cross-section of the guide groove is in a semicircular or polygonal shape.

The forming of the tip may include forming a plurality of tips to be supported by a base, and providing a guide space stepped based on the tip to the base.

According to some example embodiments, it is possible to adjust a volume of a micro-needle required for melting and to adjust an administration time by forming an artificial guide groove on the outer surface of the micro-needle. That is, it is possible to adjust an amount of medicine to be delivered based on a height and a volume of a guide groove with respect to the microneedle.

Also, according to some example embodiments, since the guide groove enables a fixed quantity of medicine to be supplied within a fixed period of time, it is possible to contribute to enhancing a reliability of a user.

Also, according to some example embodiments, since a guide space stepped based on a tip is provided to a base, it is possible to easily deliver a large amount of medicine by a capillary phenomenon.

Also, according to some example embodiments, since a micro-needle penetrates into the skin using pressure such as air pressure, oil pressure, a spring, an electromagnetic field, and/or acupressure, it is possible to enhance a medicine delivery capability according to an enhancement in the penetration capability.

Also, according to some example embodiments, it is possible to cope with various medicine and administration conditions and to deliver a large amount of medicine by adjusting a penetration power of medicine through a condition control of the guide groove.

Also, according to some example embodiments, it is possible to protect a micro-needle from an external environment by applying waterproof coating to the micro-needle.

Other features and aspects will be apparent from the following detailed description, the drawings, and the claims.

BRIEF DESCRIPTION OF THE DRAWINGS

These and/or other aspects, features, and advantages of the invention will become apparent and more readily appreciated from the following description of embodiments, taken in conjunction with the accompanying drawings of which:

FIG. 4 is a table showing various modification examples of a guide groove of FIG. 1;

FIGS. 11(a)-(e) illustrates a process of manufacturing a micro-needle corresponding to the tip forming operation of FIG. 10.

DETAILED DESCRIPTION OF THE INVENTION

Figure 1:
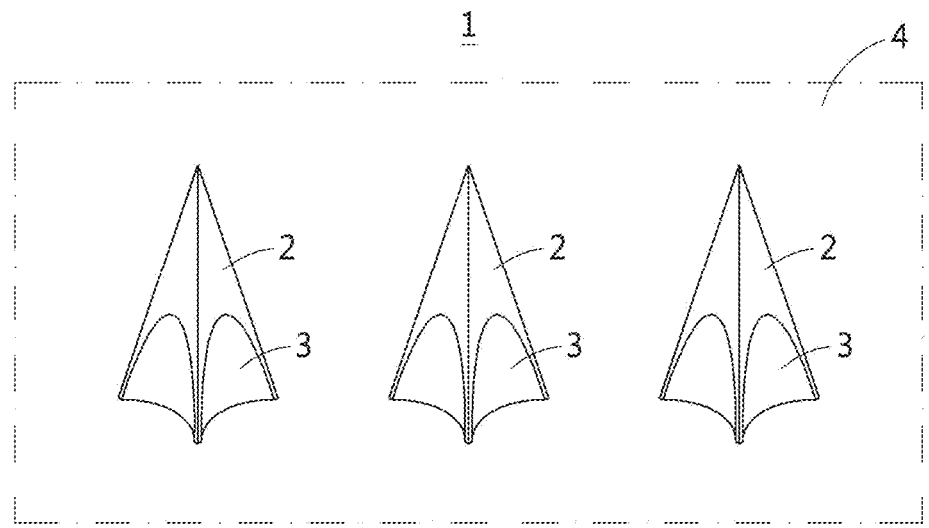
FIG. 1 is a perspective view illustrating a micro-needle according to an example embodiment.

Hereinafter, example embodiments will be described with reference to the accompanying drawings. Herein, thicknesses of lines, sizes of constituent elements, etc., illustrated in the drawings, may be exaggerated for clarity and convenience of description. Further, terms described in the following are ones defined based on functions in the present disclosure and thus, may vary based on the intent of a user or an operator, or custom. Accordingly, the definition of such terms should be made based on the overall description disclosed in the present specification.

Although the terms "first," "second," "third," etc., may be used herein to describe various elements, components, regions, layers, and/or sections, these elements, components, regions, layers, and/or sections, should not be limited by these terms. These terms are only used to distinguish one element, component, region, layer, or section, from another region, layer, or section. Thus, a first element, component, region, layer, or section, discussed below may be termed a second element, component, region, layer, or section, without departing from the scope of this disclosure.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

Hereinafter, example embodiments will be described with reference to the accompanying drawings.

Figure 2:
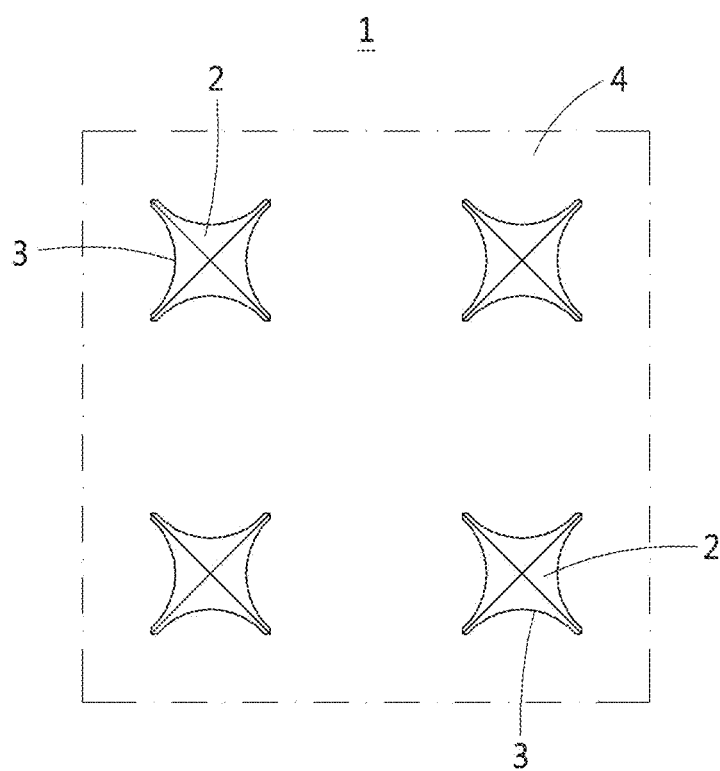
FIG. 2 is a top view illustrating the micro-needle of FIG. 1.
Figure 3:
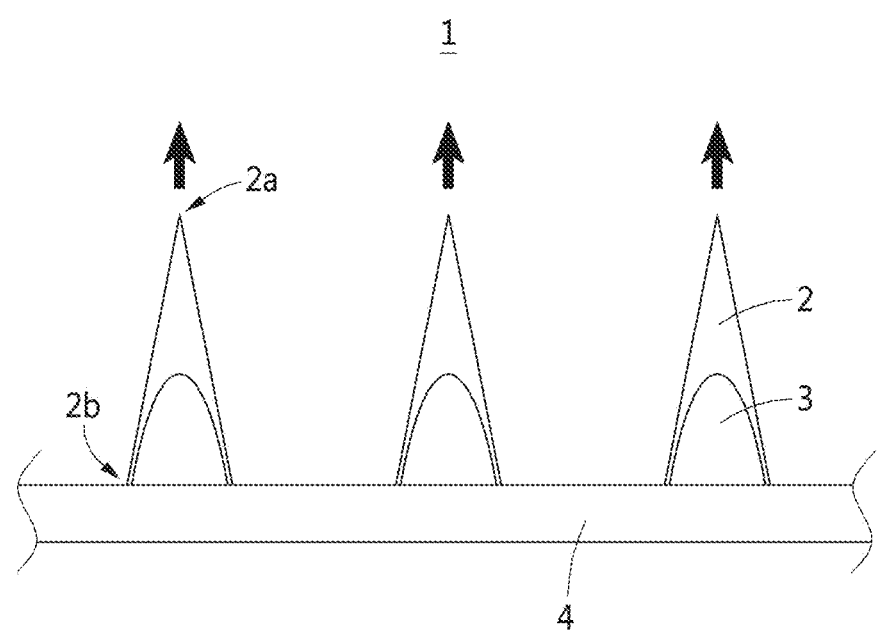
FIG. 3 is a side view of the micro-needle of FIG. 1.
Figure 5:
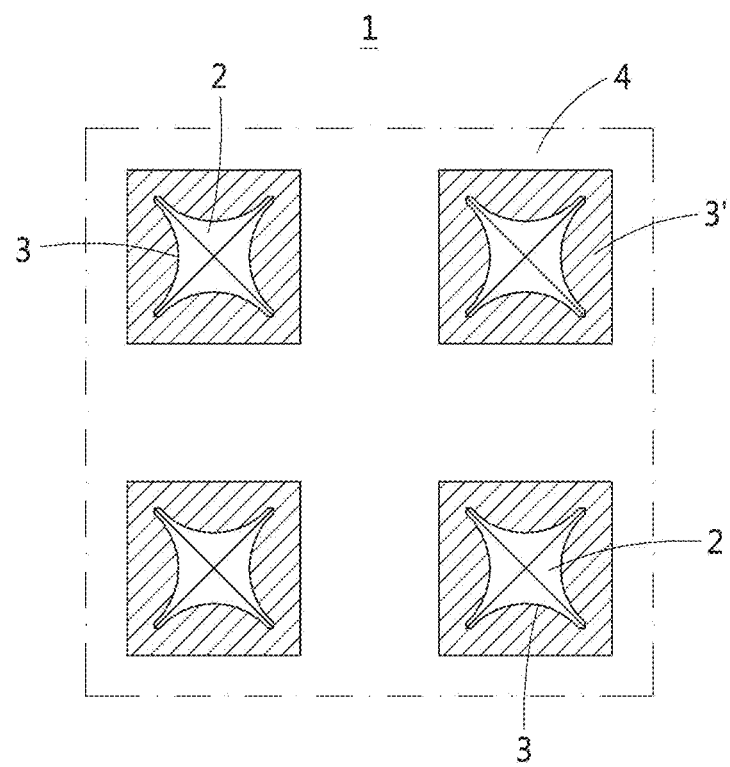
FIG. 5 is a top view illustrating a micro-needle including a guide space shown in (i) of FIG. 4.

FIG. 1 is a perspective view illustrating a micro-needle according to an example embodiment, FIG. 2 is a top view illustrating the micro-needle of FIG. 1, and FIG. 3 is a side view of the micro-needle of FIG. 1.

Referring to FIGS. 1 through 3, the micro-needle 1 according to an example embodiment includes a tip 2 and a guide groove 3.

The tip 2 is formed using medicine that penetrates into the skin and melts therein. At least one tip 2 is provided and an end of the tip 2 is in a sharp shape to facilitate penetration into the skin (see FIG. 6).

Although the present example embodiment illustrates that the tip 2 is provided in an approximate circular conic shape or polygonal conic shape and a plurality of tips 2 is provided, it is only an example and the present disclosure is not limited thereto. The plurality of tips 2 is supported by a base 4.

The guide groove 3 is in a stepped shape inward from the outer surface of the tip 2, and at least one guide groove 3 is provided to the tip 2. The guide groove 3 is configured to guide the tip 2 to penetrate into the skin and to inject a fixed quantity of medicine within a relatively short period of time.

According to the present example embodiment, a plurality of tips 2 each in a quadrangular pyramidal shape is provided on the base 4 to be spaced apart from each other. A plurality of guide grooves 3 is formed along the outer circumference of the tip 2 and each guide groove 3 has a cross-section in a semicircular shape. In more detail, referring to FIGS. 1 and 2, four guide grooves 3 are formed on four surfaces of the tip 2 in the quadrangular pyramidal shape, respectively. Also, referring to FIG. 3, the guide groove 3 is in a pillar shape that extends toward a rear end 2b between a front end 2a at which the tip 2 penetrates into the skin and the rear end 2b that extends from the front end 2a, based on a direction (see a direction of an indicator with arrowhead) in which the tip 2 penetrates into the skin. Here, the present example embodiment illustrates that the cross-section of the guide groove 3 is in the semicircular shape, for example, a starfish shape, as shown in FIG. 2.

However, the shape of the guide groove 3 and the number of guide grooves 3 are not limited to the examples of FIGS. 1 through 3. Various modification examples of FIG. 4 may be applicable to the guide groove 3.

Figure 4:
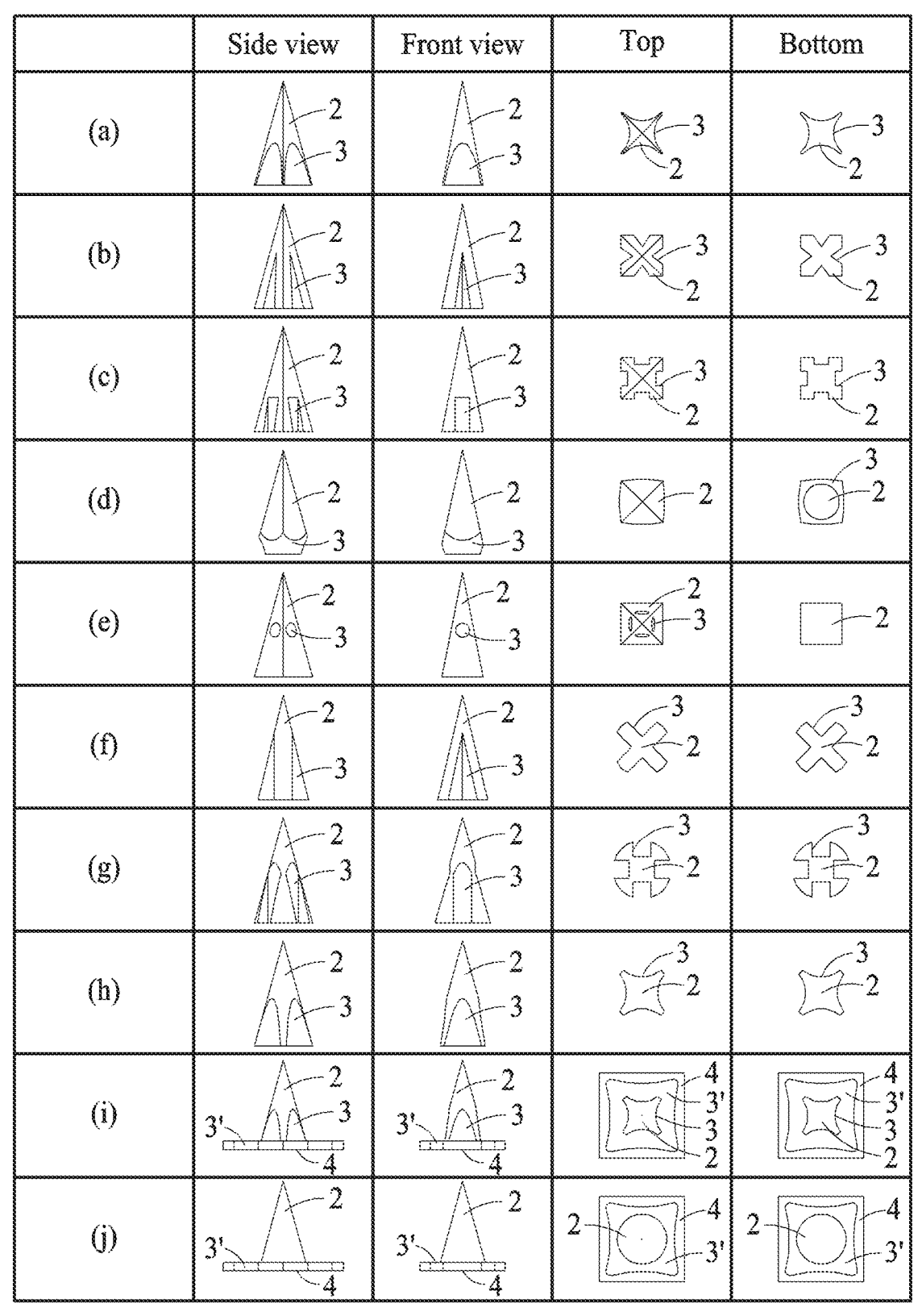

As described above with reference to FIGS. 1 through 3, (a) of FIG. 4 shows a modification example in which the guide groove 3 has a semicircular cross-section, and extends toward the rear end 2b between the front end 2a and the rear end 2b. Likewise, (b) and (c) of FIG. 4 show modification examples in which the guide groove 3 extends toward the rear end 2b between the front end 2a and the rear end 2b of the tip 2 and has a triangular or rectangular cross-section.

(d) of FIG. 4 shows a modification example in which the guide groove 3 has a semicircular cross-section and extends along the outer circumference of the tip 2. Here, the guide groove 3 is formed along the outer circumference of the rear end 2b of the tip 2. Since the guide groove 3 extends along the outer circumference of the tip 2 as above, the cross-section of the guide groove 3 may be formed in a polygonal shape.

(e) of FIG. 4 shows a modification example in which the guide groove 3 has a semicircular cross-section between the front end 2a and the rear end 2b of the tip 2 in a rectangular pyramidal shape and is formed as a plurality of inwardly stepped grooves. Even in this case, the cross-section of the guide groove 3 may be formed in a polygonal groove shape.

(f), (g), and (h) of FIG. 4 show modification examples in which the guide groove 3 having a triangular cross-section, the guide groove 3 having a rectangular cross-section, and the guide groove 3 having a semicircular cross-section are provided to the tip 2 in a circular conic shape. (f), (g), and (h) of FIG. 4 show modification examples in which the guide groove 3 has a pillar shape that extends toward the rear end 2b between the front end 2a and the rear end 2b of the tip 2.

(i) of FIG. 4 shows a modification example in which a stepped guide space 3' is provided to the base 4 based on the tip 2 together with the guide groove 3. That is, the guide space 3' may be provided together with the guide groove 3 in various shapes of (a) through (h) of FIG. 4. In addition, (j) of FIG. 4 shows a modification example in which the guide space 3' that is a stepped space is provided to the base 4 instead of forming the guide groove 3 on the tip 2.

Referring to (i) of FIG. 4, the guide space 3' that is a groove space based on the tip 2 is provided to the base 4. Thus, it is possible to deliver a large amount of medicine due to a capillary phenomenon when the tip 2 penetrates into the skin. In detail, since the guide space 3' is coated or filled with valid medicine corresponding to medicine used to form the tip 2, even medicine present in the guide space 3' may be efficiently delivered to the inside of a body due to a capillary phenomenon occurring in the guide groove 3 when inserting the tip 2 into the skin.

Although not illustrated in detail, a plurality of guide grooves 3 may be spaced apart from each other along the outer circumference of the tip 2 and provided in a multi-column and multi-row form as another modification example.

The guide groove 3 may have the aforementioned various modification examples. The guide groove 3 may be provided to an area in which the tip 2 penetrates into the skin and is to be separated. Within a few seconds after the micro-needle 1 is inserted into the skin, the tip 2 may be separated by body fluid and valid medicine may be quantitatively delivered. That is, an amount of valid medicine to be delivered may be adjusted based on a height and a volume of the tip 2 to which the guide groove 3 is provided.

The tip 2 may extend from the base 4 with a length of, desirably, 90 μm to 800 μm within the range of about 50 μm to 2000 μm. The volume of the guide groove 3 provided to the tip 2 may be adjusted based on a length ratio of the tip 2. Desirably, the guide groove 3 may be formed to have a height and a volume suitable for an amount of medicine to be delivered to a start point of the front end 2a or a location separate from the front end 2a toward the rear end 2b by 80% or more. In addition, the volume of the guide space 3' described with (i) and (j) of FIG. 4 may be adjusted to be in proportion to an interval between the tips 2. A depth of the guide space 3' may include the rear end 2b of the tip 2 or may be 1 μm to 900 μm. Desirably, the depth of the guide space 3' may be limited to 50 m to 300 μm.

Figure 6:
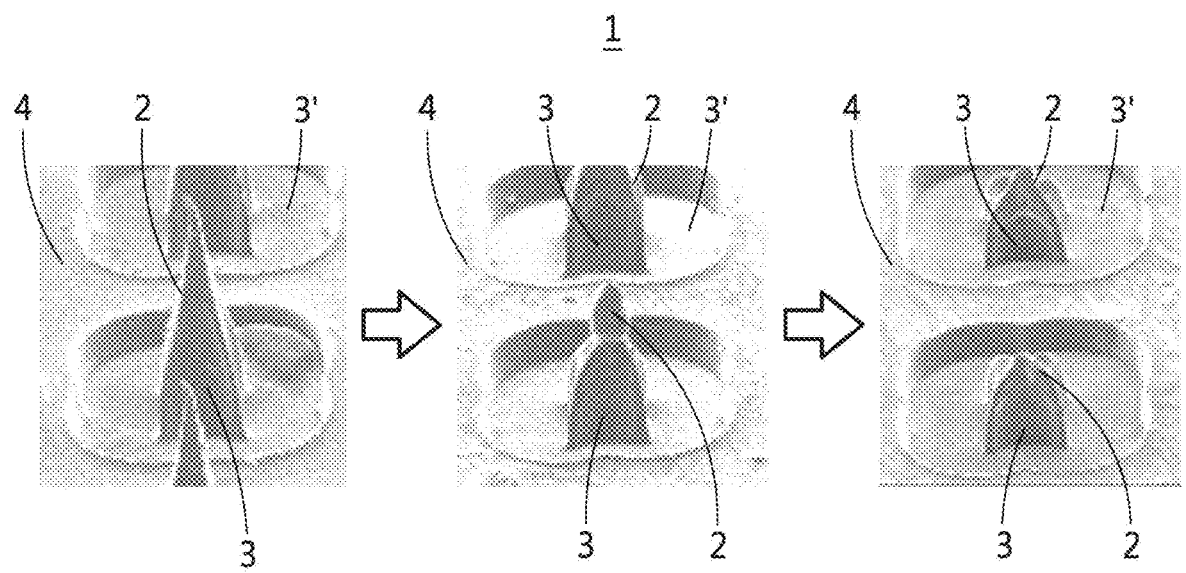
FIG. 6 illustrates sequential images about a state in which the micro-needle of FIG. 5 penetrates into the skin.

Referring to images observed with a microscope of FIG. 6, in the tip 2 to which the guide groove 3 and the guide space 3' are provided, since an end portion of the front end 2a of the tip 2 on which valid components are concentrated is separated to be in the skin, it is possible to secure the quantitative supply of medicine. That is, since the guide groove 3 guides separation of the tip 2 penetration into the skin, the quantitative supply of medicine may be guided.

Figure 7A:
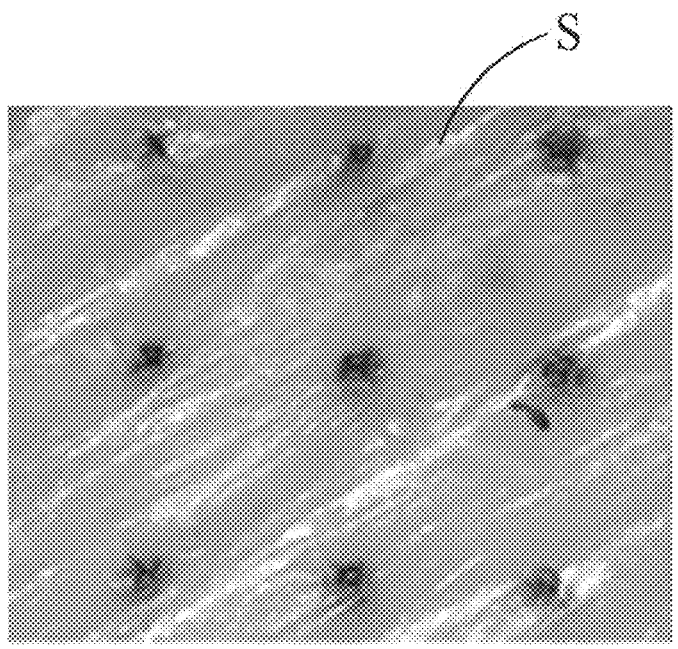
FIGS. 7A and 7B are comparison images showing a state in which a conventional micro-needle and the micro-needle of FIG. 1 penetrate into the skin.
Figure 7B:
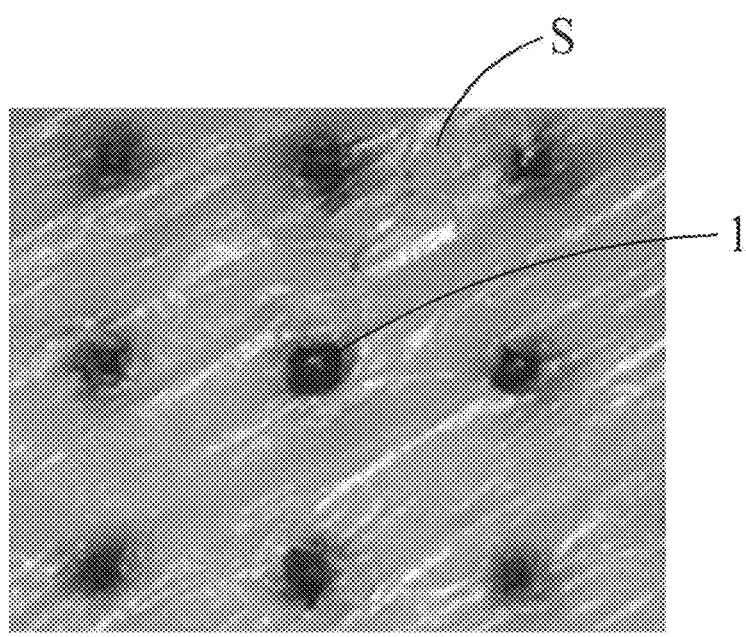

FIG. 7A is an image in which an existing micro-needle not having the guide groove 3 penetrates into the skin S, and FIG. 7B is an image in which the proposed micro-needle 1 having the guide groove 3 penetrates into the skin S. By comparing the images of FIGS. 7A and 7B, it can be known that the proposed micro-needle 1 has shown an enhanced penetration capability compared to the existing micro-needle.

In more detail, the following Table 1 shows that the micro-needle 1 including the guide groove 3 has delivered a relatively great amount of medicine compared to the existing micro-needle not having the guide groove 3. The following Table 1 shows a comparison result value about an amount of medicine delivered after the micro-needle 1 penetrates into the skin S at the pressure of 0.2 MPa through an air pressure cylinder.

TABLE 1

| | Existing micro-needle | Proposed micro-needle |
|---|---|---|
| Amount of medicine delivered after penetration | 19.0794 ± 5.3957 μg | 45.3766 ± 2.2990 μg |

Figure 8:
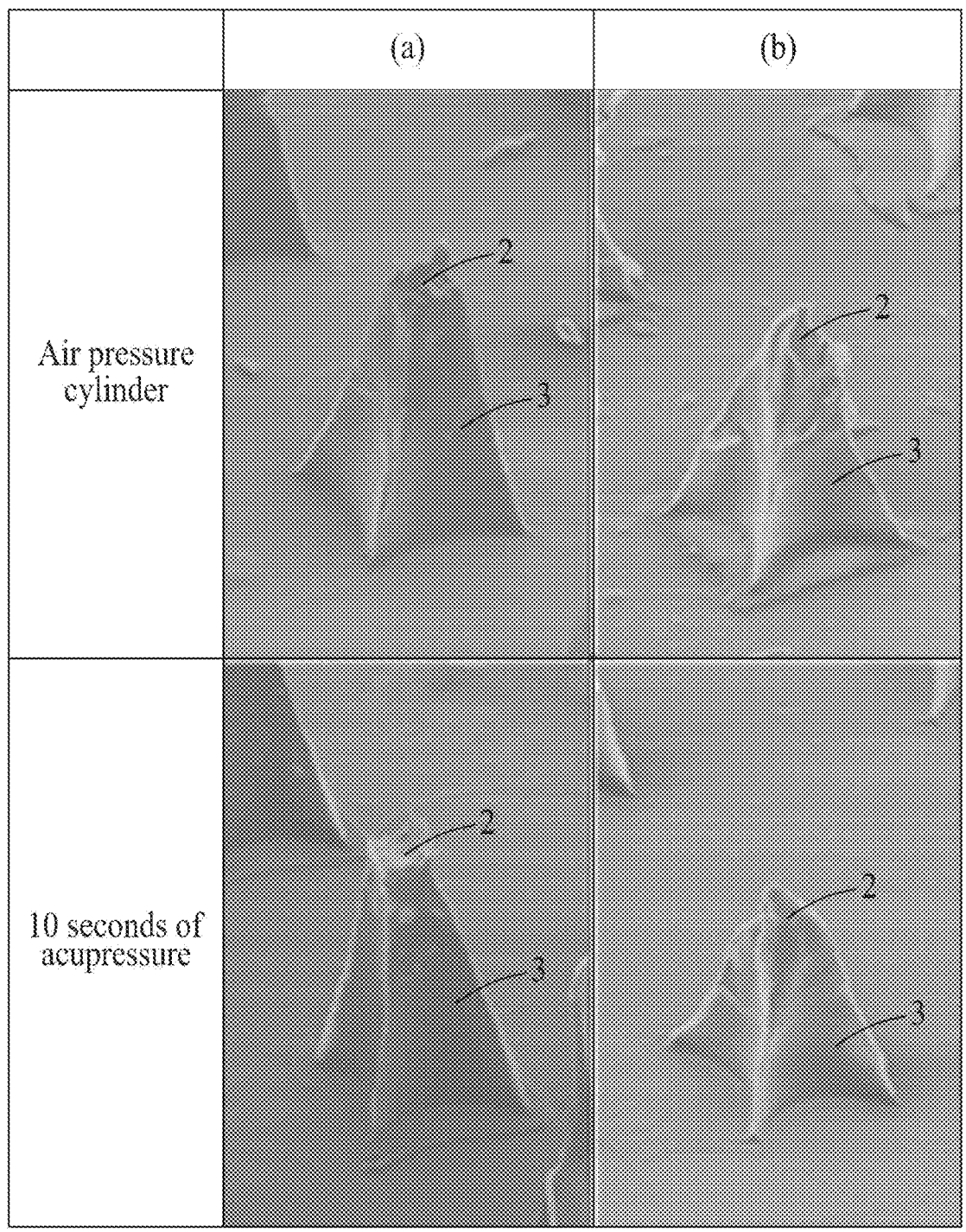
FIG. 8 is a table showing comparison images showing a state in which the micron-needle of FIG. 1 penetrates into the skin using an air pressure cylinder and acupressure.

Although not illustrated in detail, the tip 2 may penetrate into the skin through at least one of air pressure, oil pressure, a spring, an electromagnetic field, and an acupressure. Referring to FIG. 8, an image in which the tip 2 has penetrated into the skin using an air pressure cylinder and an image in which the tip 2 has penetrated into the skin at the pressure of an acupressure for 10 seconds are compared. Here, (a) of FIG. 8 shows an example in which the guide groove 3 is provided at a location tilted toward the front end 2a based on the base 4, and (b) of FIG. 8 shows an example in which the guide groove 3 is provided at a location tilted toward the rear end 2b based on the base 4.

Referring to FIG. 8, the tips 2 to which the guide grooves 3 are provided at different heights, respectively, were inserted at the force of 0.2 MPa using the air pressure cylinder and the acupressure for 10 seconds, respectively. Remaining portions of the tips 2 were compared. As a result, it can be known that the tip 2 of the proposed micro-needle 1 was efficiently separated based on the height and the volume of the guide groove 3 provided to the tip 2 of the micro-needle 1. That is, since a separation area of the tip 2 varies based on the grooved height of the guide groove 3, it is possible to efficiently adjust an amount of medicine to be delivered.

Hereinafter, a method of manufacturing the micro-needle 1 including the guide groove 3 according to an example embodiment will be described with reference to FIGS. 9 through 11.

Figure 9:
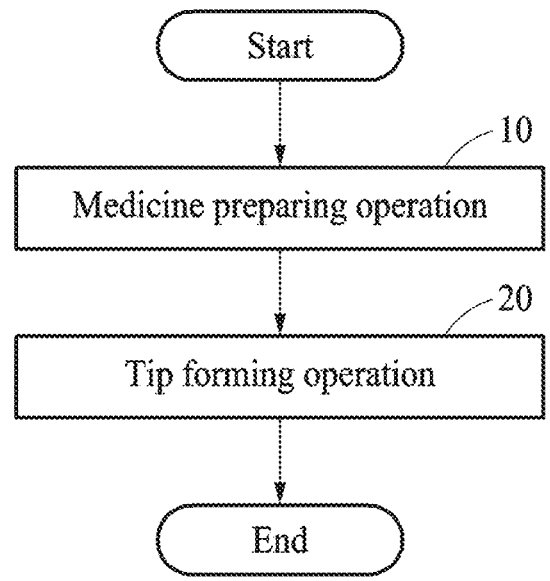
FIG. 9 is a flowchart illustrating a method of manufacturing a micro-needle according to an example embodiment.

Referring to FIG. 9, the method of manufacturing the micro-needle 1 according to an example embodiment includes a medicine preparing operation 10 and a tip forming operation 20.

In the medicine preparing operation 10, medicine 7 for forming the micro-needle 1 is prepared. Here, the medicine 7 is a mixed solution in which a biocompatible material and a water-soluble additive agent are mixed, and is in a low viscosity state or a high viscosity state.

According to the example embodiment, the biocompatible material of the medicine 7 may include at least one of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide, poly vinyl pyrrolidone (PVP), hydroxypropyl methyl cellulose (HPMC), ethylcellulose (EC), hydroxypropyl cellulose (HPC), carboxymethyl cellulose, cyclodextrin, maltose, lactose, trehalose, cellobiose, isomaltose, and turanose, and, or may include at least one of copolymer of monomers constituting the polymer, and cellulose.

Also, the water-soluble additive agent mixed in the medicine may include at least one of trehalose, oligosaccharide, sucrose, maltose, lactose, cellobiose, hyaluronic acid, alginic acid, pectin, carrageenan, chondroitin (sulfate), dextran (sulfate), chitosan, polylysine, collagen, gelatin, carboxymethyl chitin, fibrin, agarose, poly vinyl pyrrolidone (PVP), polyethylene glycol (PEG), polymethacrylate, hydroxypropyl methyl cellulose (HPMC), ethylcellulose (EC), hydroxypropyl cellulose (HPC), carboxymethyl cellulose, cyclodextrin, and gentiobiose.

Once the medicine 7 is prepared, the tip 2 is formed using the prepared medicine 7 in the tip forming operation 20. Referring to FIG. 10, the tip forming operation 20 includes a medicine filling operation 21, a solidifying operation 22, and a mold removing operation 23.

In the medicine filling operation 21, the medicine 7 is supplied to a mold 5 to which tip grooves 6 are prepared and fills in the tip grooves 6. Here, the tip groove 6 has a shape corresponding to a shape of the tip 2 of the micro-needle 1 to be manufactured.

Here, the mold 5 may include a structure that includes one of polydimethylsiloxane (PDMS), a type of polymer used for the mold, polyurethane, metal, an aluminum biocompatible material, water-soluble polymer, fat-soluble polymer, and amphiphilic polymer. The fat-soluble polymer and the amphiphilic polymer may include at least one of hydroxypropyl cellulose (HPC), hydroxypropyl methyl cellulose (HPMC), polycaprolactone (PCL), polyglycolide (PGA), polylactic acid (PLA), poly lactic-co-glycolic acid (PLGA) polymer, poly vinyl pyrrolidone (PVP), polyethylene glycol (PEG), poly ethylene oxide (PEO), poly propylene oxide (PPO), poly vinyl methyl ether (PVME), PMA (poly (methyl) acrylate)s, propylene glycol, poly (ester amide), poly (butyric acid), acrylamide (acrylic amide), acrylic acid, hyaluronic acid (HA), and gelatin.

Referring to (a) of FIG. 11, the mold 5 includes the plurality of tip grooves 6 each corresponding to a shape of the tip 2 of the micro-needle 1. Referring to (b) and (c) of FIG. 11 corresponding to the medicine filling operation 21 of FIG. 10, once the medicine 7 is supplied to the mold 5, the supplied medicine 7 is distributed to and thereby fills in the plurality of tip grooves 6.

Figure 10:
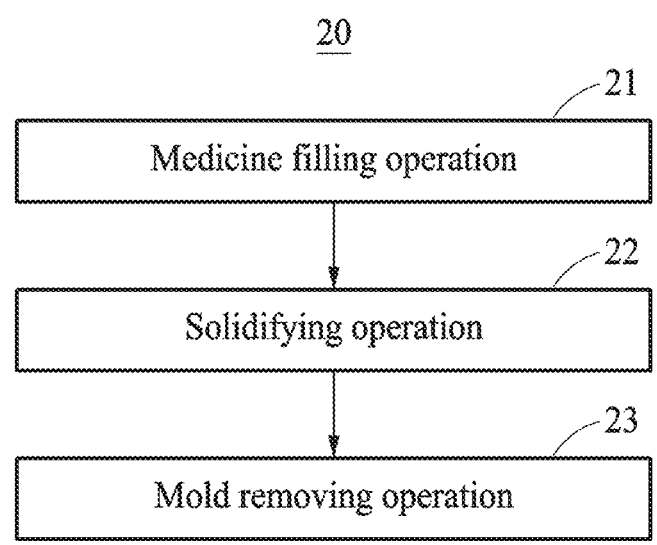
FIG. 10 is a flowchart illustrating a tip forming operation in the micro-needle manufacturing method of FIG. 9.

Referring to (d) of FIG. 11 corresponding to the solidifying operation 22 of FIG. 10, the medicine 7 filled in the tip grooves 6 is solidified. In the solidifying operation 22, the low viscous or high viscous fluid 7 filled in the plurality of tip grooves 6 forms the guide groove 3 and the medicine 7 is solidified through a centrifugal separation and polymer melt process.

As the medicine 7 is solidified, the tip 2 extends from the base 4 and the guide groove 3 is formed along the outer circumference of the tip 2 as shown in (d) of FIG. 11. Referring to (e) of FIG. 11 corresponding to the mold removing operation 23 after the solidifying operation 22, the mold 5 is removed and the manufacturing of the micro-needle 1 is completed.

Although not illustrated in detail, a waterproof coating operation of uniformly coating the surface of the micro-needle 1 with a waterproof agent is provided to protect materials sensitive to a moisture or to protect the micro-needle 1 against a moisture environment. In the waterproof coating operation, the micro-needle 1 from which the mold 5 is removed is coated with a waterproof agent using at least one of dip-coating, atomization, electro-spinning, and ultrasonic coating. Herein, the micro-needle 1 is coated with a waterproof agent through electron-spinning and then is dried at a room temperature.

Here, the waterproof agent may include a hydrophobic material or a lipid-based material. In more detail, the waterproof agent may include at least one of beeswax, oleic acid, soy fatty acid, castor oil, phosphatidylcholine, d-α-tocopherol/vitamin E, corn oil mono-di-tridiglycerides, castor oil, corn oil, cottonseed oil, olive oil, peanut oil, peppermint oil, safflower oil, sesame oil, soybean oil, hydrogenated vegetable oil, hydrogenated soybean oil, caprylic/capric triglycerides derived from coconut oil or palm see oil, phosphatidylcholine, polyethylene (PE), polypropylene (PP), polytetrafluoroethylene (PTFE), polymethylmethacrylate (PMMA), ethylene vinyl acetate (EVA), polycaprolactone (PCL), polyurethane (PU), polyethylene terephthalate (PET), polyethylene glycol (PEG), polyvinyl alcohol (PVA), poly lactide (PLA), poly lactic-co-glycolic acid (PLGA) polymer, polyglycolide (PGA), wax (paraffin cholesterol), glycerin, chitin, lecithin, animal beef tallow, vegetable stearin, low-grade saturated fatty acid, monosaturated fatty acid, tristearins, fatty acid mineral salt (zinc, calcium, magnesium stearate), and fatty acid zinc salt (stearic acid, palmitic acid, lauric acid), or may include the mixture thereof.

Although a few example embodiments have been shown and described, the present disclosure is not limited to the described embodiments. Instead, it would be appreciated by those skilled in the art that changes may be made to these embodiments without departing from the principles and spirit of the disclosure, the scope of which is defined by the claims and their equivalents.

What is claimed is:

1. A micro-needle comprising: a base; and
a plurality of tips disposed on the base with the plurality of tips being spaced apart from each other, wherein each of the plurality of tips includes:
a tip formed using medicine that penetrates into a skin and melts in the skin; and
a plurality of guide grooves provided to the tip,
wherein the tip includes a front end, a plurality of outer surfaces and a bottom, and extends from the front end to the bottom along a first direction,
wherein the tip is in a quadrangular pyramidal shape from the front end to a portion between the front end and the bottom,
wherein each of the plurality of outer surfaces is in a shape of a triangle when viewed from a side in a second direction perpendicular to the first direction and extends from the front end to the bottom,
wherein each of the plurality of guide grooves is in a shape of a step formed inwardly from an outer surface of the plurality of outer surfaces and extends from the portion between the front end and the bottom to the bottom,
wherein a cross section of each of the plurality of guide grooves is in a shape of a recess formed inwardly from the outer surface of the plurality of outer surfaces, and
wherein a size of the recess of the cross section in each of the plurality of guide grooves increases from the portion between the front end and the bottom toward the bottom along the first direction,
wherein the tip is supported by the base,
wherein the base includes an upper side and a lower side opposite to the upper side, the base not having a hole penetrating from the upper side to the lower side,
wherein a stepped groove space is provided in the upper side of the base and is formed by a recessed surface of the base,
wherein the bottom of the tip is disposed on the recessed surface of the base, and
wherein the stepped groove space is coated or filled with medicine corresponding to the medicine used to form the tip, the medicine in the stepped groove space being delivered to the inside of the skin when the tip is inserted into the skin.

2. The micro-needle of claim 1, wherein each of the plurality of guide grooves is provided along an outer circumference of each of the plurality of tips.

3. The micro-needle of claim 1, wherein the plurality of guide grooves are provided at equal intervals along an outer circumference of the tip.

4. The micro-needle of claim 1, wherein the plurality of guide grooves are spaced apart from each other at equal intervals.

5. The micro-needle of claim 1, wherein the plurality of guide grooves are spaced apart from each other along an outer circumference of the tip and provided in a multi-column and multi-row form.

6. The micro-needle of claim 1, wherein the tip penetrates into the skin using at least one of air pressure, oil pressure, spring, electromagnetic field, and acupressure.

7. The micro-needle of claim 1, wherein waterproof coating is applied to the tip.

8. A method of manufacturing a micro-needle, the method comprising:
preparing medicine; and
forming a plurality of tips and a base by supplying the medicine to a mold having a plurality of tip grooves,
wherein a plurality of inwardly stepped guide grooves are formed on each tip of the plurality of tips,
wherein the tip includes a front end, a plurality of outer surfaces and a bottom, and extends from the front end to the bottom along a first direction,
wherein the tip is in a quadrangular pyramidal shape from the front end to a portion between the front end and the bottom,
wherein each of the plurality of outer surfaces is in a shape of a triangle when viewed from a side in a second direction perpendicular to the first direction and extends from the front end to the bottom,
wherein each of the plurality of guide grooves is in a shape of a step formed inwardly from an outer surface of the plurality of outer surfaces and extends from the portion between the front end and the bottom to the bottom, and
wherein a cross section of each of the plurality of guide grooves is in a shape of a recess formed inwardly from the outer surface of the plurality of outer surfaces,
wherein a size of the recess of the cross section in each of the plurality of guide grooves increases from the portion between the front end and the bottom toward the bottom along the first direction,
wherein the tip is supported by the base,
wherein the base includes an upper side and a lower side opposite to the upper side, the base not having a hole penetrating from the upper side to the lower side,
wherein a stepped groove space is provided in the upper side of base and is formed by a recessed surface of the base,
wherein the bottom of the tip is disposed on the recessed surface of the base,
wherein the stepped groove space is coated or filled with medicine corresponding to the medicine used to form the tip, the medicine in the stepped groove space being delivered to the inside of the skin when the tip is inserted into the skin.

9. The method of claim 8, wherein the preparing of the medicine comprises preparing the medicine using a biocompatible material and a water-soluble additive agent.

10. The method of claim 9, wherein the biocompatible material includes at least one of carboxymethyl cellulose (CMC), hyaluronic acid, alginic acid, pectin, carrageenan, chondroitin (sulfate), dextran (sulfate), chitosan, polylysine, carboxymethyl chitin, fibrin, agarose, pullulan, polyanhydride, polyorthoester, polyetherester, polyesteramide, poly (butyric acid), poly (valeric acid), polyacrylate, ethylene-vinyl acetate polymer, acrylic substituted cellulose acetate, polyvinyl chloride, polyvinylidene fluoride, poly (vinyl imidazole), chlorosulphonate polyolefins, polyethylene oxide, poly vinyl pyrrolidone (PVP), hydroxypropyl methyl cellulose (HPMC), ethylcellulose (EC), hydroxypropyl cellulose (HPC), carboxymethyl cellulose, cyclodextrin, maltose, lactose, trehalose, cellobiose, isomaltose, and turanose, or includes at least one of copolymer of monomers constituting the polymer, and cellulose.

11. The method of claim 9, wherein the water-soluble additive agent includes at least one of trehalose, oligosaccharide, sucrose, maltose, lactose, cellobiose, hyaluronic acid, alginic acid, pectin, carrageenan, chondroitin (sulfate), dextran (sulfate), chitosan, polylysine, collagen, gelatin, carboxymethyl chitin, fibrin, agarose, poly vinyl pyrrolidone (PVP), polyethylene glycol (PEG), polymethacrylate, hydroxypropyl methyl cellulose (HPMC), ethylcellulose (EC), hydroxypropyl cellulose (HPC), carboxymethyl cellulose, cyclodextrin, and gentiobiose.

12. The method of claim 8, wherein the mold includes a structure that includes one of polydimethylsiloxane (PDMS), used for the mold, polyurethane, metal, an aluminum biocompatible material, water-soluble polymer, fat-soluble polymer, and amphiphilic polymer.

13. The method of claim 12, wherein the mold includes at least one of hydroxypropyl cellulose (HPC), hydroxypropyl methyl cellulose (HPMC), polycaprolactone (PCL), polyglycolide (PGA), polylactic acid (PLA), poly lactic-co-glycolic acid (PLGA) polymer, poly vinyl pyrrolidone (PVP), polyethylene glycol (PEG), poly ethylene oxide (PEO), poly propylene oxide (PPO), poly vinyl methyl ether (PVME), PMA (poly (methyl) acrylate)s, propylene glycol, poly (ester amide), poly (butyric acid), acrylamide (acrylic amide), acrylic acid, hyaluronic acid (HA), and gelatin.

14. The method of claim 8, wherein the forming of the plurality of tips comprises:
supplying the medicine to the plurality of tip grooves;
solidifying the medicine; and
removing the mold,
wherein the solidifying comprises forming the plurality of guide grooves through a centrifugal and polymer melt process, and solidifying the medicine.

15. The method of claim 8, further comprising:
applying waterproof coating to the plurality of tips.

16. The method of claim 8, wherein the applying of the waterproof coating comprises coating an end of each of the plurality of tips or the entire surface of each of the plurality of tips with a waterproof agent that includes a hydrophobic material or a lipid-based material using at least one of dip-coating, atomization, electro-spinning, and ultrasonic coating.

17. The method of claim 16, wherein the waterproof agent includes at least one of beeswax, oleic acid, soy fatty acid, castor oil, phosphatidylcholine, d-α-tocopherol/vitamin E, corn oil mono-di-tridiglycerides, castor oil, corn oil, cottonseed oil, olive oil, peanut oil, peppermint oil, safflower oil, sesame oil, soybean oil, hydrogenated vegetable oil, hydrogenated soybean oil, caprylic/capric triglycerides derived from coconut oil or palm see oil, phosphatidylcholine, polyethylene (PE), polypropylene (PP), polytetrafluoroethylene (PTFE), polymethylmethacrylate (PMMA), ethylene vinyl acetate (EVA), polycaprolactone (PCL), polyurethane (PU), polyethylene terephthalate (PET), polyethylene glycol (PEG), polyvinyl alcohol (PVA), poly lactide (PLA), poly lactic-co-glycolic acid (PLGA) polymer, polyglycolide (PGA), wax (paraffin cholesterol), glycerin, chitin, lecithin, animal beef tallow, vegetable stearin, low-grade saturated fatty acid, monosaturated fatty acid, tristearins, fatty acid mineral salt (zinc, calcium, magnesium stearate), and fatty acid zinc salt (stearic acid, palmitic acid, lauric acid), or includes the mixture thereof.

* * * * *